(12) United States Patent  (10) Patent No.: US 9,267,880 B1
Tan et al.  (45) Date of Patent: *Feb. 23, 2016

(54) RING-DOWN BINNING IN FSR HOPPING MODE

(71) Applicant: Picarro, Inc., Santa Clara, CA (US)

(72) Inventors: Sze Meng Tan, Santa Clara, CA (US); John A. Hoffnagle, San Jose, CA (US); Chris W. Rella, Sunnyvale, CA (US)

(73) Assignee: Picarro, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/634,682

(22) Filed: Feb. 27, 2015

Related U.S. Application Data

(63) Continuation-in-part of application No. 14/037,908, filed on Sep. 26, 2003, now Pat. No. 8,982,352.

(60) Provisional application No. 61/833,807, filed on Jun. 11, 2013.

(51) Int. Cl.
*G01N 21/61* (2006.01)
*G01N 21/25* (2006.01)
*G01N 21/39* (2006.01)

(52) U.S. Cl.
CPC .............. *G01N 21/255* (2013.01); *G01N 21/39* (2013.01); *G01N 2201/06113* (2013.01)

(58) Field of Classification Search
CPC .............. G01N 21/1702; G01N 21/39; G01N 2021/391; G01J 3/42; G01J 3/28; H01S 3/1392
USPC ............................. 356/437, 326, 243.1–243.8
See application file for complete search history.

(56) References Cited

U.S. PATENT DOCUMENTS

| | | | | |
|---|---|---|---|---|
| 4,925,302 | A * | 5/1990 | Cutler | 356/128 |
| 7,450,240 | B2 | 11/2008 | Morville et al. | |
| 8,982,352 | B1 * | 3/2015 | Hoffnagle et al. | 356/437 |
| 2002/0130252 | A1 * | 9/2002 | Funakawa | 250/226 |
| 2003/0210715 | A1 * | 11/2003 | Lokai et al. | 372/20 |
| 2008/0137089 | A1 * | 6/2008 | Tan | 356/454 |

OTHER PUBLICATIONS

Motto-Ros et al, "Mode by mode optical feedback: cavity ringdown spectroscopy", 2007, Applied Physics B v87 pp. 531-538.

* cited by examiner

*Primary Examiner* — Hoa Pham
(74) *Attorney, Agent, or Firm* — Lumen Patent Firm

(57) ABSTRACT

For cavity enhanced optical spectroscopy, the cavity modes are used as a frequency reference. Data analysis methods are employed that assume the data points are at equally spaced frequencies. Parameters of interest such as line width, integrated absorption etc. can be determined from such data without knowledge of the frequencies of any of the data points. Methods for determining the FSR index of each ringdown event are also provided.

14 Claims, 11 Drawing Sheets

RING-DOWN BINNING IN FSR HOPPING MODE

CROSS REFERENCE TO RELATED APPLICATIONS

This application is a continuation in part of U.S. Ser. No. 14/037,908, filed Sep. 26, 2013, and hereby incorporated by reference in its entirety.

U.S. Ser. No. 14/037,908 claims the benefit of U.S. provisional patent application 61/833,807, filed on Jun. 11, 2013, and hereby incorporated by reference in its entirety.

FIELD OF THE INVENTION

This invention relates to optical spectroscopy.

BACKGROUND

Spectroscopic measurements of quantities of interest (e.g., gas concentration) often rely on spectroscopic measurements at several frequencies. One common example is determination of gas concentration from a measured spectral absorption line of the gas. Here the integrated absorption over the spectral line can be used to determine the gas concentration.

Cavity enhanced optical spectroscopy makes use of an optical resonator to improve instrument performance. Cavity ring-down spectroscopy (CRDS) is one such method, where cavity energy decay times (i.e., cavity ring-down times) are measured in order to determine the absorption provided by a sample. In such instruments, it is important to consider the effect of the cavity modes on spectral absorption data. For example, in CRDS two operating modes have been considered in the art.

In the first CRDS operating mode, the optical source frequency is held at a nominally fixed value and the length of the cavity is varied such that cavity modes sweep through the source frequency, thereby generating ring-down events at the fixed source frequency. This operating mode can be referred to as a swept cavity mode. Spectral data in the swept cavity mode is obtained by tuning the source to the desired frequencies and sweeping the cavity length long enough at each of these source frequencies until sufficient data has been collected.

In the second CRDS operating mode, the cavity length is held at a nominally fixed value and the frequency of the source is varied such that the source frequency sweeps through one or more of the cavity mode frequencies, thereby generating ring-down events at the cavity mode frequencies. This operating mode can be referred to as a swept source mode. A single source frequency sweep in this mode provides absorption data points at frequencies that are spaced by the free spectral range (FSR) of the cavity. Measures to increase resolution in this mode have been employed. For example, the cavity length can be changed between successive source frequency sweeps such that frequency resolution is improved.

In either case, the resulting raw data for this kind of measurement generally has data points that are measurements at various frequencies (e.g., $(v, \alpha(v))$ pairs, where $v$ is frequency and $\alpha(v)$ is absorption at that frequency). Errors in the frequency $v$ of these data points can undesirably reduce the accuracy of the final determination of gas concentration.

It would be an advance in the art to provide spectroscopic methods that are less reliant on accurate frequency values in absorption data.

SUMMARY

The main idea of the present approach is to use the cavity modes as a quasi-frequency reference. More specifically, the cavity is constructed to passively provide sufficient frequency stability that:

1) for any single ring-down spectrum acquisition, which can be referred to as a spectrogram, the cavity frequencies are equally spaced by the FSR.

However, 2) from one spectrum acquisition to another, the cavity frequencies can change, although the FSR remains (approximately) constant.

Thus the cavity defines a frequency comb. The comb is substantially fixed in position during acquisition of a spectrogram, but the phase of the comb can drift in frequency space over time between spectrogram acquisitions.

Raw spectrograms are processed to provide outputs (e.g., concentrations, concentration ratios, etc.) using methods that do not need an absolute frequency scale for the data, but instead merely assume the data points are equally spaced in frequency (by the FSR, which often doesn't have to be known).

FIGS. 1 and 2 schematically illustrate this point. FIG. 1 shows conventional spectral absorption data, where each data point has an absorption value (e.g., $\alpha(v_1)$) and an associated frequency (e.g., $v_1$). FIG. 2 shows spectral absorption data as considered in the present work. Here each data point has an absorption value (e.g., $\alpha_2$) and an associated index (e.g., 2) that identifies the associated cavity mode. No frequency values for individual data points are considered or available in such a data set. Instead, as indicated above, it is assumed that the cavity is sufficiently stable during data acquisition that it defines a fixed comb of equally spaced frequencies.

We have found, surprisingly, that for many purposes it is not necessary to have $(v, \alpha(v))$ data points as in FIG. 1, and instead it suffices to have data as in FIG. 2. This discovery can be better appreciated by considering the computation of integrated spectral absorption from raw data. A conventional approach for this would be to perform measurements at points that are spaced significantly closer to each other than the line width of the feature being measured, e.g., as shown on FIG. 3. Numerical integration of such data would provide a reasonable estimate of the integrated absorption.

Attempting to obtain accurate integrated absorption results for data as in FIG. 2 would therefore appear to face two main obstacles: 1) for practical cavity dimensions, the frequency resolution provided by the cavity FSR tends to be comparable to line widths of feature of interest, which would appear to be inadequate resolution; and 2) knowledge of the frequencies would appear to be essential to compute the spectrally integrated absorption.

FIG. 4 shows an exemplary answer to the first problem identified above. For a spectral line of a given width, (as measured by its half-width at half maximum, denoted by HWHM), FIG. 4 shows how well its strength may be determined by distributing a fixed total number of absorption measurements amongst a whole number of uniformly spaced frequencies ranging from −5 HWHM to +5 HWHM around the peak. Once the spacing is comparable to the HWHM, there is little to be gained by using more finely spaced frequencies.

The answer to the second problem identified above is to avoid the use of numerical integration to determine integrated absorption. Instead, a line shape model is fitted to the data, assuming data points equally spaced in frequency, and the integrated absorption is determined from the fitting parameters (such as amplitude, line width, etc.). Such fitting can give an accurate absolute value for integrated absorption if the cavity FSR is known, and can give an accurate relative value of integrated absorption if the cavity FSR is not known. Thus the only frequency value that is used is the FSR, and even that minimal level of frequency information is not needed in all cases.

As described in greater detail below, the main motivation for this approach is that relying on frequency values in the data (as in FIG. 1) means that inaccurate frequency values will introduce corresponding errors in the final results such as integrated absorption. As a practical matter it is very difficult and costly to ensure sufficient accuracy for these frequency values. Avoidance of such cost and difficulties is the main advantage of the present approach. Methods for determining the FSR index of each ring-down event are also provided.

DETAILED DESCRIPTION

In section A, some general principles relating to embodiments of the invention are considered. Section B is an extended example where these principles are considered in connection with cavity ring-down spectroscopy. Section C describes methods for determining the FSR index of each ring-down event.

A) General Principles

Figure 5:
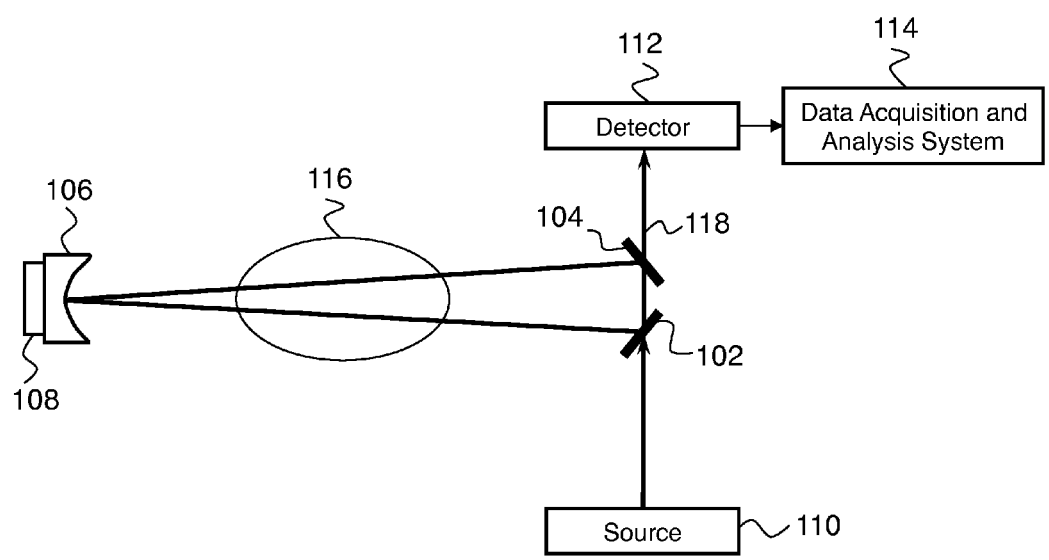
FIG. 5 shows an exemplary system suitable for practicing embodiments of the invention.

FIG. 5 shows an exemplary system for cavity enhanced spectroscopy suitable for practicing embodiments of the invention. Exemplary cavity enhanced spectroscopy methods include, but are not limited to: cavity ring-down spectroscopy, cavity enhanced absorption spectroscopy, and integrated cavity output spectroscopy. An optical resonator formed by mirrors 102, 104 and 106 defines a first set of cavity modes having a free spectral range (FSR). The optical resonator is configured to include a sample 116 for analysis, and is also configured to passively provide relative frequency stability of the first set of cavity modes of 10% or less of the FSR in a time period of about 1 second. More preferably, the relative frequency stability of the first set of cavity modes is 1% or less of the FSR in a time period of about 1 second. Still more preferably, the relative frequency stability of the first set of cavity modes is 0.1% or less of the FSR in a time period of about 1 second. Most preferably, the relative frequency stability of the first set of cavity modes is 0.01% or less of the FSR in a time period of about 1 second. Preferably, the optical resonator is disposed in an environment having actively stabilized temperature and pressure. Improving the frequency stability of the cavity increases the accuracy of the assumption of equally spaced frequencies that is made in data analysis.

Preferably, the first set of cavity modes are fundamental TEM00 modes. Alternatively, the first set of cavity modes can include one or more higher order transverse modes. Preferably, the optical resonator has a confocal geometry, such that frequency combs relating to different transverse modes are substantially aligned with each other. The optical resonator can have any optical or geometrical configuration suitable for use in connection with cavity enhanced spectroscopy, including but not limited to: standing wave resonator and ring resonator.

An optical source 110 is configured to deliver optical radiation to the optical resonator. In some embodiments, it is preferred for the optical source to provide relative frequency stability of the optical radiation of 10% or less of the FSR in a time period of about 1 second. In other embodiments, it is preferred for the optical source to provide relative frequency precision of the optical radiation of 10% or less of the FSR in a time period of about 1 second. A stable optical source can be used without needing a wavelength monitor, while a precise but unstable source can be used in connection with a wavelength monitor. A detector 112 is configured to receive an absorbance signal 118 from the optical resonator that is responsive to optical absorption in the sample. Optionally, the position of one or more cavity mirrors can be adjustable (e.g., piezoelectric transducer 108 on mirror 106).

In operation, data acquisition and analysis system 114 collects spectrograms from the sample 116 by sweeping a frequency of the optical source 110 through two or more frequencies of the first set of cavity modes and recording the absorbance signal. An analysis output from the spectrogram is computed by assuming that data points in the spectrogram are evenly spaced in frequency, without any reference to absolute frequencies of the data points.

Sweeping a frequency of the optical source through two or more frequencies of the first set of cavity modes can include dithering the frequency of the optical source around frequencies of two or more selected cavity modes to obtain one or more raw measurements at each of the selected cavity modes. The selected cavity modes can have equal numbers of raw measurements or different numbers of raw measurements.

Frequency control of the optical source can be used to facilitate tuning the frequency of the optical source to align with two or more of the first set of cavity modes when collecting spectrogram. In cases where the optical source is a semiconductor laser, the frequency control of the optical source can include both current control and temperature control.

Computing an analysis output can include determining an integrated absorption by fitting a spectral line shape model to the spectrogram. The analysis output can be a spectrally integrated concentration, an isotopic ratio, and/or a spectral line width of an analyte line.

Figure 10:
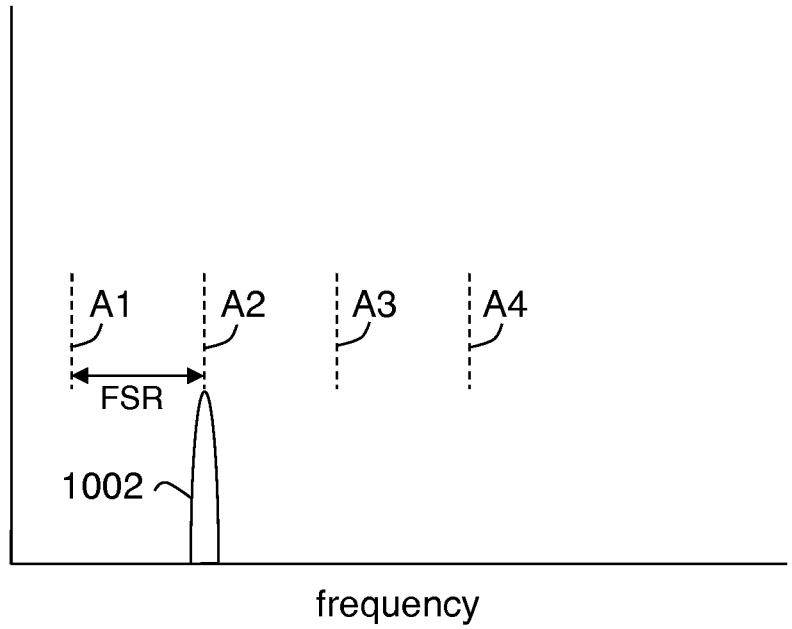
FIG. 10 shows the effect of locking a comb of cavity modes to a frequency reference.
Figure 11:
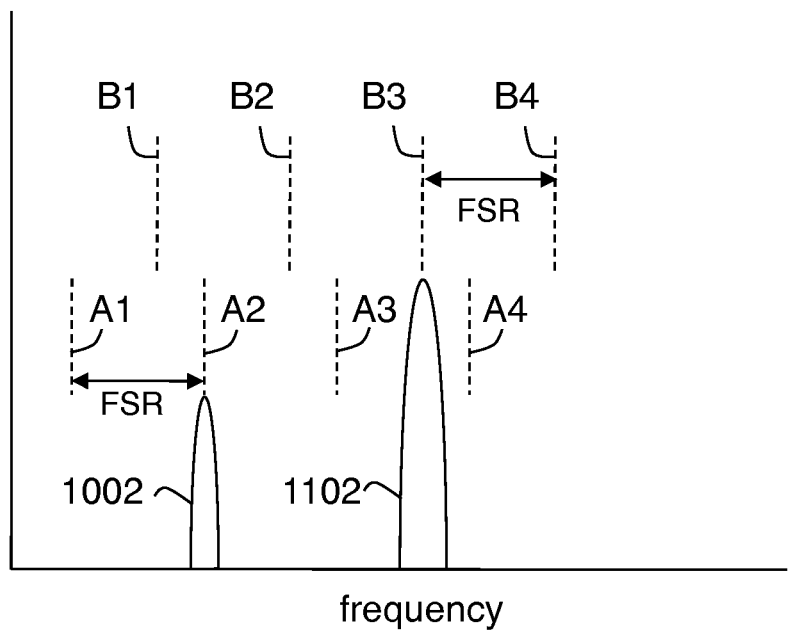
FIG. 11 shows the effect of locking two distinct combs of cavity modes to two frequency references.

The optical path length of the cavity can be controlled to align the cavity mode frequency comb to a frequency reference. Such a reference can be a spectroscopic feature of the sample. FIG. 10 shows an example. Multiple frequency references can be employed. For example, an optical path length of the optical resonator can be adjustable to two or more values in operation to define at least a second set of cavity modes distinct from the first set of cavity modes. If two or more sets of cavity modes are defined, they can each have their own frequency references. For example, the first set of cavity modes can be locked to a first frequency reference, and the second set of cavity modes can be locked to a second frequency reference. Spectroscopic features of the sample can provide multiple frequency references. FIG. 11 shows an example of this.

B) Exemplary CRDS Design Considerations

B1) Introduction

The cavity ring-down technique is an exceptionally sensitive means to determine the loss of a high-finesse optical cavity, including any optical absorbers present in the beam path defined by the cavity. The ring down method is combined with a tunable light source in cavity ring-down spectroscopy (CRDS). Measurements of cavity loss at multiple frequencies in the neighborhood of a molecular absorption line or lines permit the detection of trace amounts of absorbing species in a gas sample enclosed in the cavity. In order to derive a quantitative measurement of the concentration of the absorbing species from the ring-down loss, accurate and stable knowledge of the optical frequencies at which the CRDS measurements were made is usually regarded as being essential.

We describe a means of injecting light from a laser into an optical cavity which has the advantages of considerable freedom in choosing the optical frequencies at which data points are acquired and high speed of data acquisition, while using the ring-down cavity itself as a very stable local frequency standard. This approach exploits the precision with which the distribution of cavity resonance frequencies is known when the length of the cavity is kept fixed, in order to improve the stability of each absorption measurement. Accurate frequency values for absorption data points are not necessary. We show how the spectra acquired with the CRDS spectrometer, operating in this manner, can be analyzed to yield precise, quantitative measurements of molecular concentrations and concentration ratios, with excellent stability over long time intervals.

B2) Spectroscopic Background

In wavelength-scanned CRDS (WS-CRDS), the quantity that is directly measured is the cavity loss and measurements are made at multiple optical frequencies to construct a loss spectrum. The loss spectrum of the empty cavity can be determined from ancillary measurements and the remaining loss is assumed to be due to linear absorption by the gas sample filling the cavity. Linear absorption in this context means absorption that follows Beer's law, $$I(z)=I_0\exp[-\alpha(v)z]$$

where $I_0$ is the optical intensity at z=0 of a uniform beam of light propagating in the positive z direction, I(z) is the intensity after propagating the distance z in the uniform absorbing medium, and $\alpha$, which is a function of optical frequency v, is the absorption coefficient. In the linear regime $\alpha$ is proportional to the number density of absorbing molecules in the cavity, and this proportionality allows one to deduce the concentration of absorbing molecules in the gas sample from the measured cavity loss.

Figure 1:
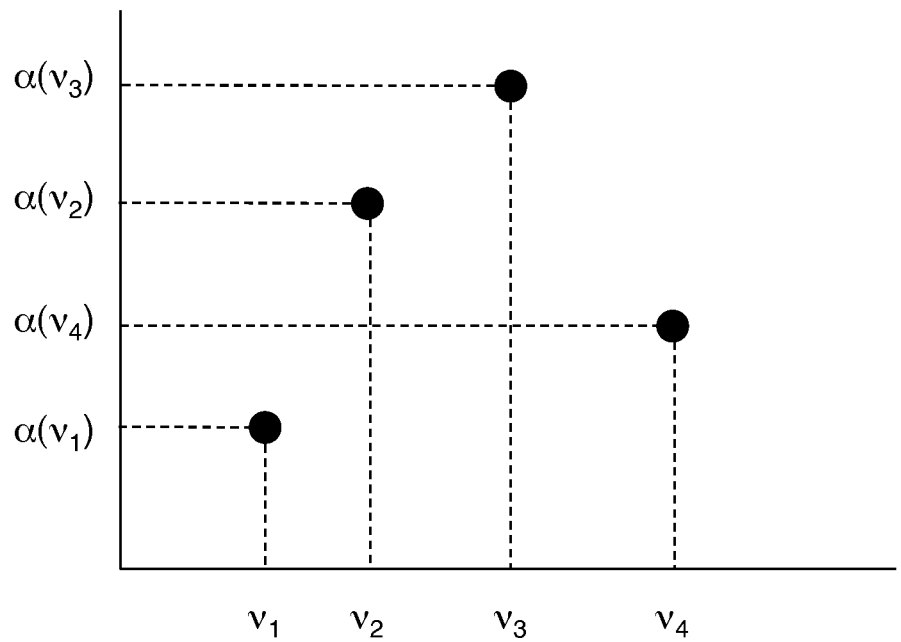
FIG. 1 schematically shows conventional spectral absorption data.
Figure 2:
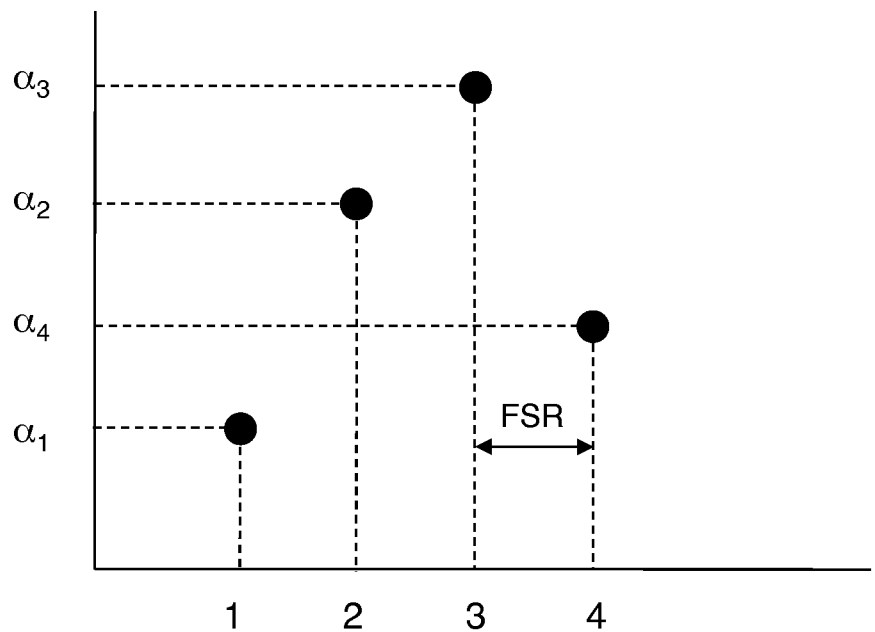
FIG. 2 schematically shows spectral absorption data as utilized in embodiments of the invention.
Figure 3:
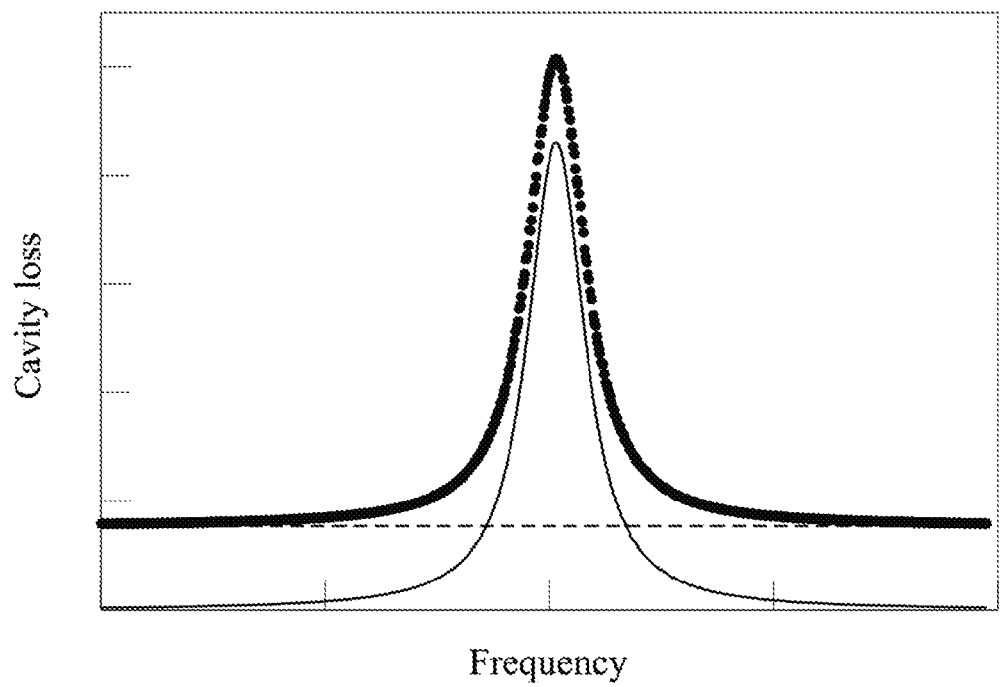
FIG. 3 is an example of absorption data.

An example of an absorption spectrum for a single, isolated spectral line is illustrated in FIG. 3. Here points are measured cavity loss values, the dashed curve is the empty cavity loss measured separately, and the solid curve is the loss due to a single spectral line. In this example, the frequency dependence of the molecular absorption is accurately described by the Galatry function of spectral line shape theory. The frequency spread of the line in FIG. 3 is determined by the conditions in which the absorbing molecules find themselves: the temperature, pressure, and composition of the surrounding gas. Regardless of the line shape, the integrated absorption, $\int_0^\infty \alpha(v)dv$, is the quantity which is proportional to molecular number density. Other measures of molecular absorption, such as the absorption at a specific frequency, depend on the line shape as well as the molecular number density. Because the integrated absorption is the quantity most directly related to molecular number density, it is especially well suited to serve as the basis of a spectroscopic determination of the composition of a gas sample. However, the computation of integrated absorption from measured WS-CRDS data depends crucially on how well one knows the frequencies of the measured loss values. Errors in the frequencies v at which the $\alpha(v)$ were measured directly affect the integrated absorption.

Figure 4:
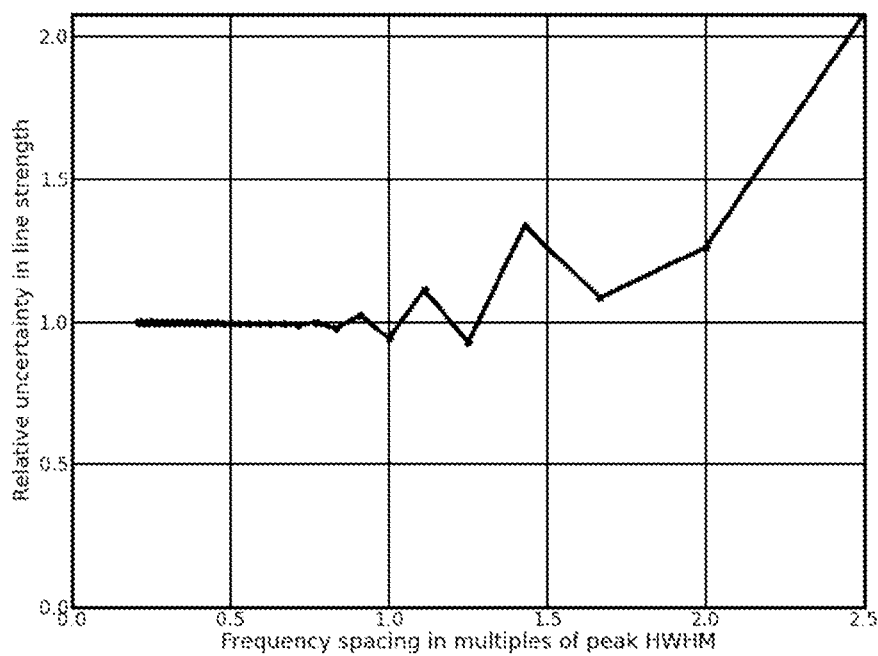
FIG. 4 shows an example of the effect of frequency resolution on parameter accuracy.

Note that as a practical matter, we do not attempt a mathematical or numerical quadrature to find the integrated absorption. Rather we use the method of least-squares fitting of measured spectral data to a model with adjustable parameters. In this procedure we derive a spectral model from careful measurements of samples of known composition. The spectral model includes the empty cavity loss and the absorption from the species to be quantified as well as other molecules than can be in the samples to be analyzed. Non-resonant absorption from strong spectral lines outside the frequency range of the measurements may also need to be included. In its final form the spectral model is a mathematical expression in terms of known functions which incorporates a number of adjustable parameters. For instance, the spectrum of FIG. 3 might be modeled as the sum of a baseline with a slope and offset and a term AG(v), where G(v) is a Galatry function normalized such that $\int_0^\infty G(v)dv=\sqrt{\pi}$, and A is a coefficient that describes the amplitude of the absorption feature. When analyzing the loss spectrum of an sample of unknown composition, a number of parameters including the coefficient A and possibly the Galatry parameters that determine the shape of the spectral line, are adjusted to minimize the sum of squares of the deviations of the model from the observed spectrum. The model spectrum with optimized adjustable parameters is then taken to be the best estimate of the true spectrum of the sample. Since the Galatry function G is defined to have area $\sqrt{\pi}$, the coefficient A is, except for unimportant constant factors, the same as the integrated absorption. An important consequence of the least-squares fitting method is that the ring-down measurements can be made at any set of optical frequencies that provides enough spectral information to constrain all the adjustable parameters in the model. Measurements do not have to be made at frequency intervals small compared to the widths of the absorption lines. For instance, although the finely spaced spectrum shown in FIG. 3 may present a human observer with the pleasing illusion of continuity, far fewer discrete frequencies are actually needed to determine the center frequency, width, and amplitude of the spectral line, as seen on FIG. 4.

B3) Improvement of the Frequency Scale for WS-CRDS

Stability and linearity of the frequency axis are directly related to the precision and drift of the WS-CRDS analyzer. Although frequency metrology is capable in principle of extraordinary precision through the use of optical frequency combs or atom-stabilized reference lasers, such technologies are much too complex and expensive to be used in field-deployable, relatively inexpensive instruments. Consequently, frequency assignments for the CRDS have in the past been made by independent calibration of the laser frequency as a function of operating temperature and current, or by an auxiliary measurement with a dispersive element such as a wavelength monitor (WLM). Both of these methods suffer from drift on time scales longer than a few minutes. We have now implemented a new technique that improves frequency precision and stability by using the CRDS cavity itself as the ultimate frequency reference.

A high-finesse optical cavity exhibits very narrow resonances at discrete frequencies labeled by transverse and longitudinal mode numbers. We take care to align the cavity and laser such that only the lowest-order transverse mode, the $TEM_{00}$ mode, is excited. The cavity resonance frequency thus depends only on the longitudinal mode number, equal to the optical phase acquired by the light beam during one round trip of the cavity, in units of $2\pi$ radians. This means that, neglecting the tiny effect of dispersion over typical CRDS frequency ranges, the modes of the cavity are equally spaced in frequency. The mode spacing is referred to as the free spectral range (FSR) of the cavity. If we choose to express frequency in units of wavenumber, $k=v/c$ where c is the speed of light in vacuum, the free spectral range is simply $$FSR=1/L$$

where L is the optical path length of the resonant mode. For a typical cavity, L=48 cm, which leads to a free spectral range that is somewhat smaller than the line width of the molecular absorption lines under typical spectroscopic conditions.

The regular comb of longitudinal modes of the CRDS cavity itself provides a frequency measuring stick that is extremely precise and stable, without adding at all to the cost or complexity of the CRDS spectrometer. By manufacturing the cavity from a low temperature coefficient material and stabilizing the temperature of the cavity, the mechanical length of the cavity mode can be kept very nearly constant. Invar, for instance, has temperature coefficient of expansion on the order of $10^{-6}$/K, and it is practical to stabilize the cavity temperature to 0.01-0.1 K, so the mechanical length of the cavity an be made stable to about $10^{-8}$-$10^{-7}$. By stabilizing the pressure of the gas in the cavity (e.g., air) the index of refraction of the medium in the cavity can be kept very nearly constant. Assuming the cavity is filled with air at an operating pressure of 140 Torr, the relative change of the cavity FSR with pressure is $2.6\times10^{-7}$/Torr. Pressure stabilization of 0.01-0.1 Torr is practical, so pressure changes contribute on the order of $10^{-8}$ to the cavity FSR. When the optical path length of the cavity is kept constant, spectra acquired at frequencies separated by integral multiples of the free spectral range can be fit to a model of absorption versus optical frequency, as described above, with frequency values that are precise and stable over long periods of time. Consequently the ultimate precision of the CRDS analyzer is improved.

To exploit the stability of the CRDS cavity as an optical frequency standard we have devised a new mode of operation for the WS-CRDS analyzer. Minimally, a means of setting and determining the frequency of the laser at the time of each ring-down is required. So long as the resolution of this determination is better than the separation between cavity resonances, it is possible to classify each ring-down measurement as occurring at the frequency of a particular resonance, and hence to determine its position in the spectrum. The method of setting the frequency of the laser so as to collect data efficiently and with sufficiently high repetition rate to allow enough measurements to be made to achieve the desired levels of precision is more challenging, and constitutes a significant aspect of this work. The ability to specify a list of frequencies at which the data are to be collected, and to specify the number of ring down events that are to be collected at each of these frequencies are key to optimizing the data collection process for a given measurement.

Figure 6:
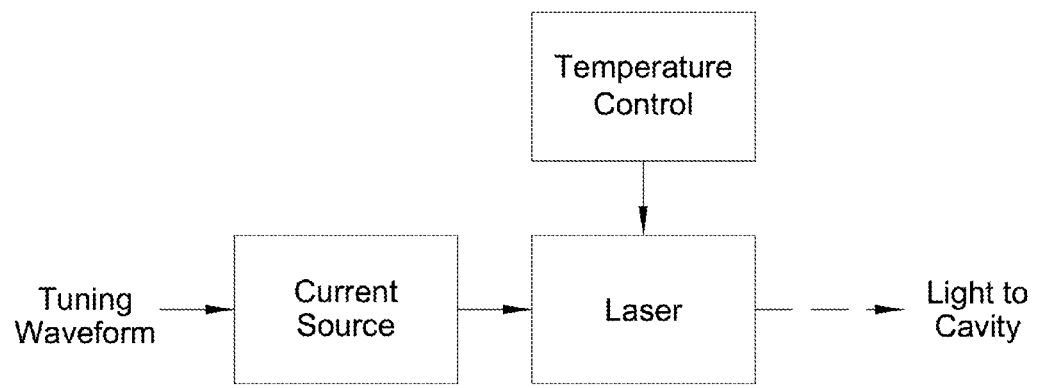
FIG. 6 is a simplified block diagram of laser control.
Figure 7:
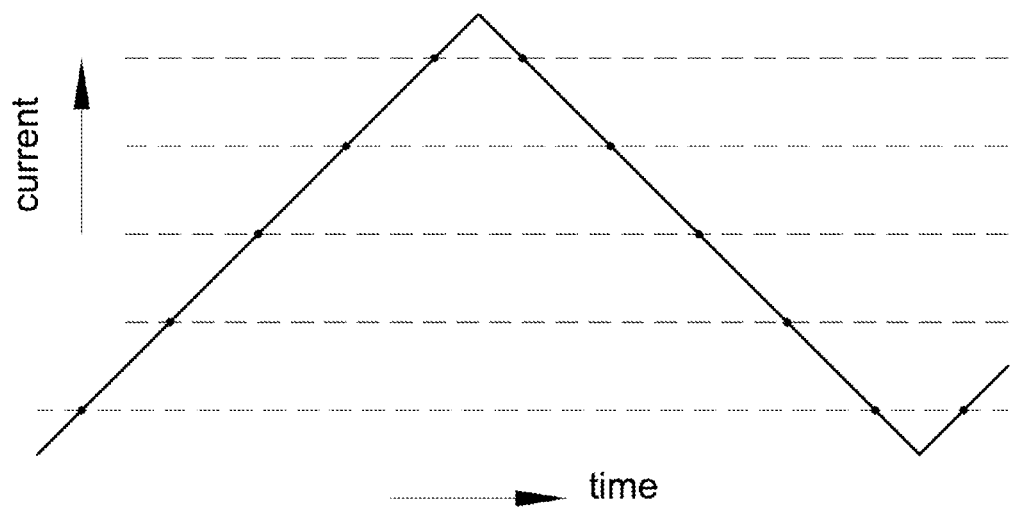
FIG. 7 schematically shows an example of laser tuning for CRDS.

Setting the frequency of a laser involves adjusting various physical parameters, depending on the details of its construction. For the purposes of this discussion, the laser temperature and current will be used as representative examples of such parameters as these are appropriate for semiconductor distributed feedback lasers. FIG. 6 is a block diagram of a portion of the laser control subsystem of a cavity ring down spectrometer using such a laser. The laser injects light into an optical cavity, and the laser temperature and current are adjusted to tune the laser to the desired frequency. When the intensity in the cavity reaches a predetermined value, a trigger signal is generated to turn off the optical injection and initiate a ring down. In the simplest approach, the laser frequency is tuned over the range of interest, for example by driving the laser current with a triangular tuning waveform of the appropriate amplitude (see FIG. 7). Assuming that the laser temperature is kept constant, its frequency will vary with the current, and the optical cavity will fill with sufficient light to allow a ring down to be initiated from time to time. In FIG. 7, the laser current values which cause the laser frequency to coincide with a cavity resonance are shown as dashed lines. Each time the laser current crosses such a line, there is an enhanced probability of cavity filling, and a ring down can occur if the amount of light within the cavity is sufficiently large. Such times are indicated by dots. The slope of the tuning waveform determines the rate at which the laser frequency is varied and in order to efficiently fill the cavity, this rate must be limited so that the light is quasi-monochromatic on the timescale of the cavity filling. In such a system, the acquisition rate will be slow, because for most of the time, the laser frequency falls between the cavity resonances during which time no filling occurs.

Figure 8:
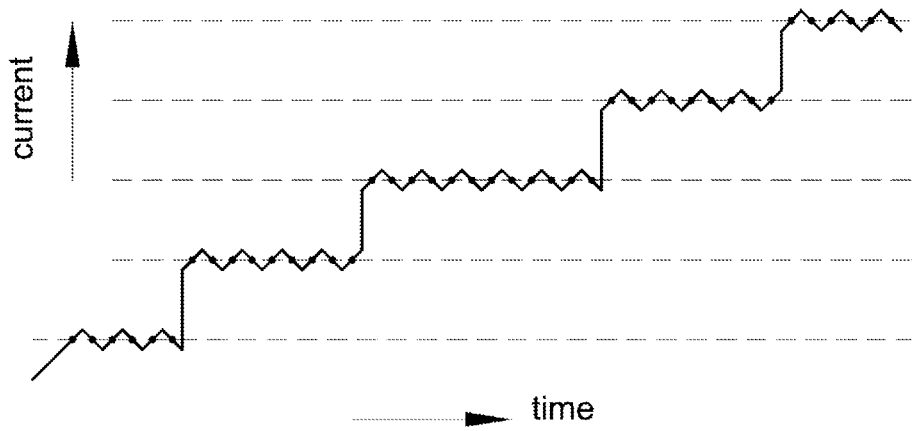
FIG. 8 schematically shows an improved approach for laser tuning for CRDS.

An improvement to the above approach is to modify the tuning waveform so that the laser does not spend much of the time tuned to frequencies at which the cavity is not resonant. If the value of the laser current is recorded at the time a successful ring down occurs, further ring downs may be collected at the same frequency by varying the current in a narrow range (dithering) around this recorded value (see FIG. 8). It is still important to keep the slope of the waveform small, to maintain filling efficiency, but so long that the range is limited to a small fraction of the separation between cavity resonances, the rate at which ring down events occur can be much larger than with the simple approach. In order to tune the laser to a different cavity resonance while maintaining the large ring down rate, the current needs to be changed quickly (shown by the vertical lines) so that it is close to the value needed to achieve the new resonant frequency before it is swept more slowly to achieve good cavity filling at this frequency. The various laser currents needed to move between cavity resonances may be predetermined and stored in a lookup table for subsequent use.

Several problems become apparent when we remember that laser current is not the only quantity that determines the frequency. If the laser temperature is not constant, the current required to bring the laser frequency into coincidence with a cavity resonance is not constant and so varying the laser current in a small range with the expectation of keeping the laser frequency correspondingly close to a cavity resonance will fail. The effect of a varying laser temperature can be visualized by imagining the dashed lines in FIGS. 7 and 8 as no longer being horizontal, but rather moving up and down as the temperature changes. If ring downs are initiated by turning off the laser current, followed by subsequently turning the laser on again to initiate a new acquisition cycle, this process results in significant temperature fluctuations and gradients within the laser which are difficult to stabilize against, since they occur at much faster timescales than are accessible to a typical thermal controller. Similarly, jumping between successive cavity modes using precomputed currents is not feasible when the laser temperature fluctuates unpredictably.

One approach to overcoming these problems is to avoid processes that change the temperature of the laser, so that its value can be maintained more precisely constant. For example, an external modulator may be used to turn off the optical injection into the cavity, rather than turning the laser off by removing or reducing the current. Although effective, the additional cost of such a modulator may render this solution less desirable for many applications. Thus it is helpful to have ways to control the laser in cases where the laser is turned off to initiate ring-downs. Another point to consider is that detuning the laser from the resonance removes much of the light from the cavity, but it doesn't eliminate it completely, and the light that remains can beat with the light in the cavity to create a time-varying signal that leads to noise on the measurement of the ring-down time. Thus detuning the laser may not be an appropriate way to initiate ring-downs, even though it does have the advantage of not significantly altering the laser temperature.

Figure 9:
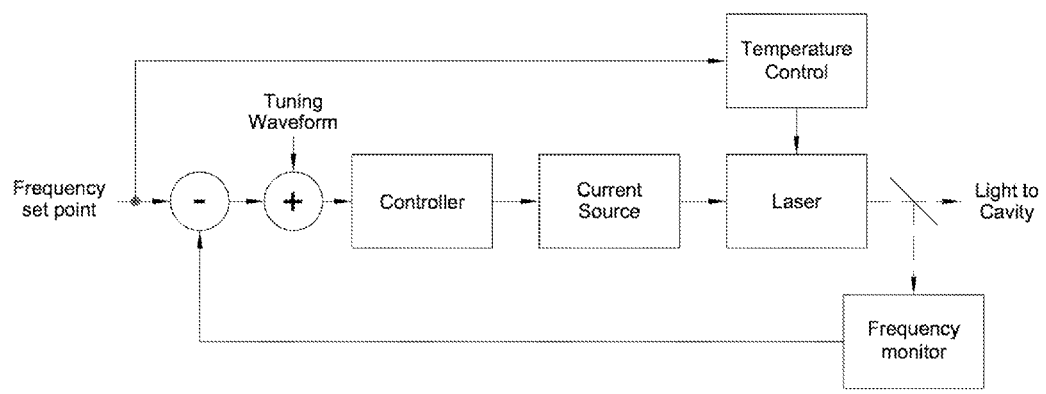
FIG. 9 is a block diagram of temperature and current control of a laser using a frequency monitor.

Another approach is to use a frequency measuring device such as described in U.S. Pat. No. 7,813,886 within a feedback loop to adjust the laser current (as shown in FIG. 9). The difference between the frequency set point and the measured frequency is the error signal, and this is used to adjust the laser current so that the laser frequency remains close to the desired value, even in the presence of laser temperature fluctuations or other external disturbances. A block implementing an algorithm such as a PID (proportional, integral and derivative) controller may usefully be introduced in order to take into account the dynamics of the feedback loop.

By specifying the frequency set points to be a collection of frequencies separated by multiples of the free spectral range of the cavity, the laser can be tuned close to the cavity resonances in a range of frequencies that generate the desired spectrum. Since the laser current can be adjusted rather quickly, and the laser frequency responds to such adjustments with very small delay, the time response of the feedback loop can be made much faster than any temperature changes. The slow tuning of the laser required to bring its frequency into precise resonance with the cavity can now be carried out by adding a triangular tuning waveform to the set point of the control loop (or equivalently to the error signal).

The method outlined above of recording the value of the tuning waveform at the time of a successful ring down event and subsequently dithering the waveform about this value is again useful for generating a rapid succession of ring down events at a single frequency. If the set point of the feedback loop is adjusted to be close to another cavity resonance, ring down events at the new frequency will occur so long that the amplitude of the triangular waveform is large enough to sweep the laser frequency through the resonance. If this is not the case, it is possible to find the new resonant frequency simply by increasing the amplitude of the tuning waveform until a ring down does occur and then switching back into the rapid dithering about this value. By introducing the tuning waveform at this position in the feedback loop, it is necessary to ramp its value over at most a single cavity free spectral range in order to bring the laser and the cavity into resonance.

A simple heuristic for switching from dithering to ramping is to do so if a ring down has not been detected for more than some length of time. With careful adjustment of the amplitude of the triangular waveform, so that it exceeds the imprecision inherent in the frequency measuring device, it is possible to make the transition to ramping occur infrequently, allowing a continuously high data acquisition rate.

Since the feedback loop now adjusts the laser current to the correct value in order to achieve a desired laser frequency, we can adjust the laser temperature so that the range of adjustment required for the laser current is reduced. This can be achieved by storing the laser temperature required to produce a given frequency when the current is at some nominal value. When it is desired to generate a particular frequency, the laser temperature control system is instructed to change the laser temperature to that value, as indicated by the line in FIG. 9 which links the temperature control block to the frequency set point. Even as the temperature is approaching the set point (on the relatively slow timescale of the thermal control loop), the laser current will be adjusted by the feedback loop to produce the correct frequency. All during this time, rapid ring down acquisition can take place, as the frequency is well controlled. Since the laser frequency can typically be tuned over a much wider range by varying the temperature than by varying the current, this allows the system to access the entire frequency range available to the laser.

Although a frequency monitor is used within the control loop, it is important to note that the frequencies at which the data are collected are still determined by the cavity resonances. Any inaccuracy or drift in the frequency monitor does not affect the quality of the measurement, so long that these do not compromise our ability to assign each ring down unambiguously to a specific resonance. Any long-term drifts can usually be compensated for by using spectroscopic information in the collected spectra, such as the frequencies of known absorption features.

The methods described above are generically referred to as laser current tuning (LCT) modes to emphasize that the laser current is used to bring the laser frequency into coincidence with a cavity resonance. With the appropriate refinements, the procedure produces a rapid sequence of ring down events for a prescribed sequence of longitudinal modes of the cavity, with the cavity length being held constant. In this way, a spectrum of cavity loss versus frequency is acquired with the property that all optical frequencies lie precisely on a comb with frequency spacing equal to the cavity FSR. If more than one molecular species is to be analyzed, it is possible to acquire a piecewise spectrum in which each spectral line of interest is covered by a comb of frequencies spaced by exactly one FSR, but the FSR-spaced pieces are shifted by an arbitrary frequency, by moving one mirror of the cavity with a piezoelectric translator (PZT). In this case each piece of the total spectrum has a stable frequency axis, by virtue of the stability of the cavity FSR, while the relative positions of the pieces are stable because they are tied to molecular absorption lines which have inherently well-defined frequencies. It is also possible to use spectroscopic fitting to inform how the length of the cavity should be changed, if it is desired to align some cavity resonance with the peak of a specific spectral line, so that many points may be collected precisely at the peak, in order to measure better the value of the absorption.

B4) Analysis of Spectra Acquired in LCT Mode

After a spectrum of loss versus frequency has been acquired, it is analyzed by least-squares fitting to a spectroscopic model, as described above. The most important difference from conventional data analysis is that the optical frequencies associated with the ring-down measurements are constrained to be spaced by multiples of the cavity FSR. The free parameters that are adjusted in the fit typically include the line amplitude A, the line width, and the center frequency of the fitted spectral line. The line amplitude is used to derive the concentration of the species of interest in the sample. The measured center frequency can be used to ensure long-term stability of the frequency scale, even though there may be slow and undetected drifts in the temperature and pressure sensors that are used to stabilize the cavity. If the fitting procedure indicates that the experimentally observed ring-downs are displaced in frequency from the requested values, a small correction is applied to the PZT to adjust the mechanical length of the cavity accordingly. In this way the optical path length can be stabilized such that a specific longitudinal mode of the cavity always has a spectroscopically fixed frequency. The PZT adjustment is applied between periods when ring-down spectra are applied, so that each spectrum is acquired with optical frequencies on an FSR grid. FIG. 10 shows an example of the resulting alignment of the frequency comb having frequencies A1, A2, A3, and A4 with a frequency reference 1002, which could be an absorption peak in the sample.

This idea of locking frequency combs to frequency references can be extended to two (or more) frequency combs and references, as shown on FIG. 11. Here the cavity length can be controlled to define a first set of cavity modes A1, A2, A3 and A4 that is locked to a first frequency reference 1002. The cavity length can also be controlled to define a second set of cavity modes B1, B2, B3, and B4 that is locked to a second frequency reference 1102. Switching between these modes can be accomplished without removing the sample from the instrument, so the ability to sequentially use multiple different frequency references can be valuable for analyzing multi-component samples.

The use of the line amplitude together with the stabilization of the frequency axis by the LCT method greatly reduces the sensitivity of the analyzer to drift or instability in the pressure control of the sample. The reasoning is slightly different for analyzers intended for concentration measurements or for stable isotope analysis. Consider isotopic analysis first. In this case it is the ratio of isotopologues of a given molecule that is of interest, more than absolute concentration. Stabilizing the frequency axis allows reproducible measurements of line strengths over long time periods, and the ratio of line strengths provides a measurement of the isotopic ratio which is independent of the cavity pressure and therefore not affected by slow drifts in the cavity pressure sensor. The result is more reproducible measurements that can be averaged for long time periods, yielding better ultimate isotopic ratio precision. When measuring the concentration of a molecular species, drift in the pressure sensor degrades measurement reproducibility, because for a given sample composition the number density of the absorbing species in the cavity is proportional to pressure as known from the ideal gas law. The improved frequency axis provided by LCT is valuable for concentration measurements because it allows a more stable, reproducible measure of the spectral line width. Since collisional broadening of the spectral line is proportional to pressure, as is the number density of molecules in a gas sample, the line width information can be used to correct for drifts in cavity pressure, thus improving the long-term reproducibility of concentration measurements.

B5) Comparison of Experimental Data

Figure 12:
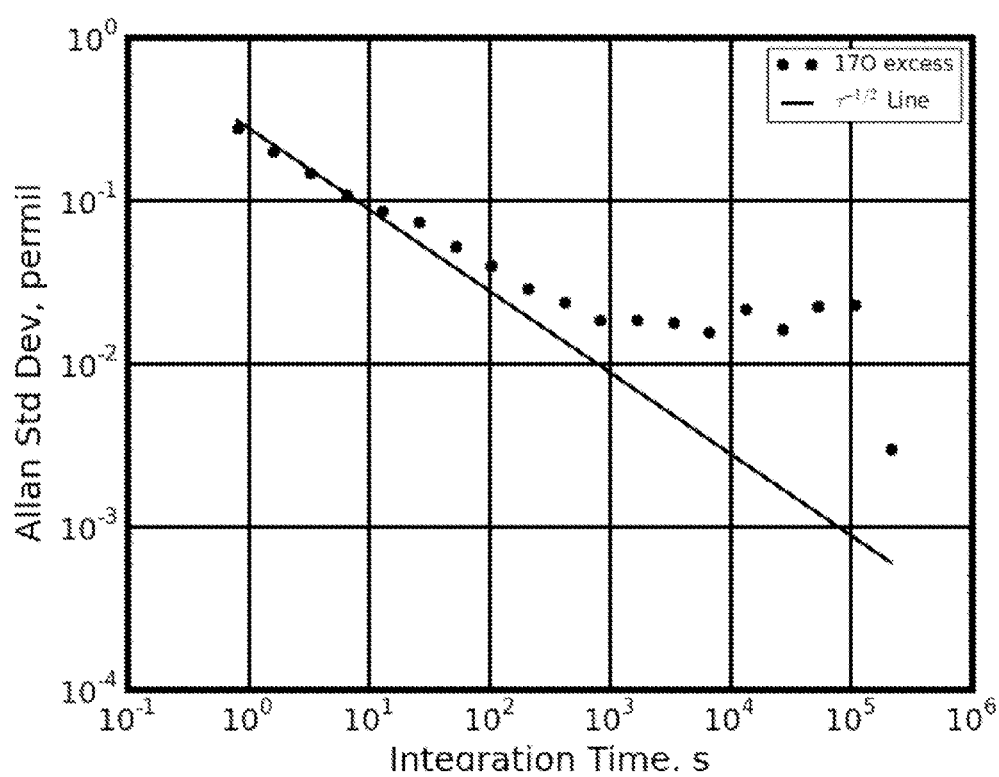
FIG. 12 shows Allan variance results for conventional CRDS.

The Allan variance provides a quantitative way of depicting the stability of a measurement method when it is used to measure repeatedly the same quantity. A wavelength scanned cavity ring down spectrometer was used to measure the relative isotopic abundance of the oxygen isotopes $^{16}O$, $^{17}O$ and $^{18}O$ in water vapor of constant composition. The analyzer was first configured to use cavity length tuning, in which the cavity length is adjusted to bring it into resonance with the laser. The laser frequency is adjusted using the frequency monitor alone as its reference. Data were collected for several days in order to determine how well the uncertainty would decrease as the measured results are averaged. FIG. 12 shows that the optimum precision achieved is about 20 per meg, after an averaging time of approximately 1000 s. Due to drifts in the system, further averaging does not improve the precision further.

Figure 13:
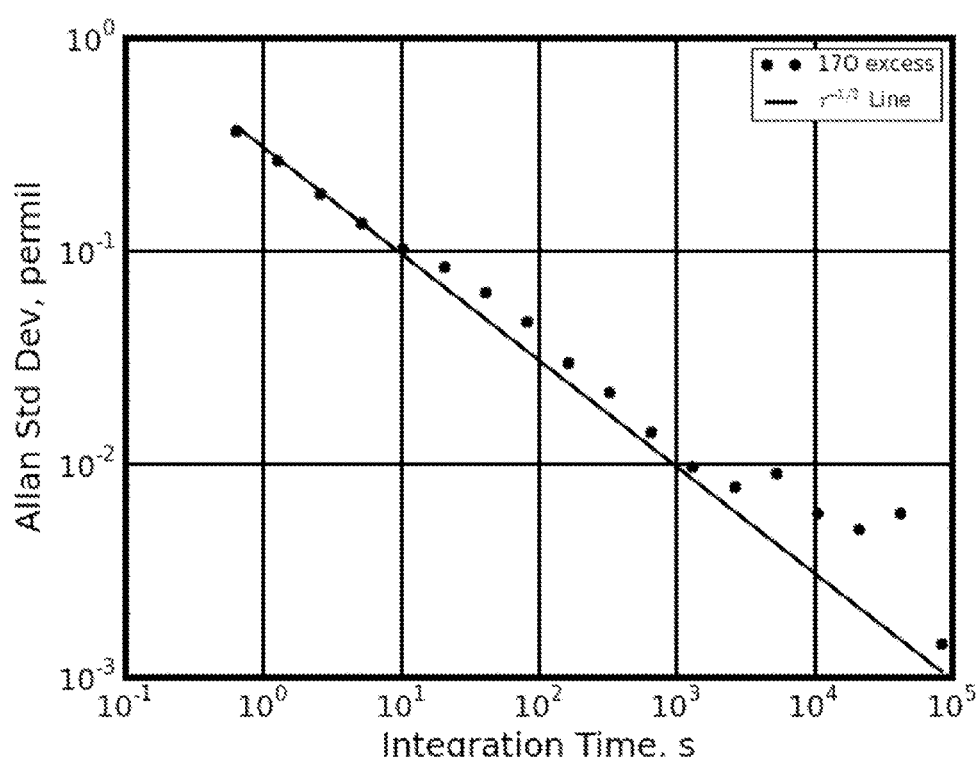
FIG. 13 shows Allan variance results corresponding to FIG. 12 when laser current tuning CRDS is employed.

When the analyzer was subsequently configured to use the enhanced laser current tuning method described above, so that the frequency axis is now calibrated using the equally spaced cavity resonances, the new Allan variance plot is as shown in FIG. 13. Averaging can now usefully be performed for timescales around 10,000 s resulting in higher precision of about 5 per meg.

B6) Conclusion

This work provides methods to:
1) Acquire WS-CRDS data using a spectrometer with a stable, high-finesse optical cavity and (optionally) an ancillary wavelength monitor, generating spectra for which the optical frequencies are directly related to the optical path length of the cavity while simultaneously permitting high measurement rate and flexible allocation of ring-down measurements at different wavelengths.
2) Analyze the WS-CRDS spectra so acquired to derive physically meaningful quantities, such as mixing ratios of gas species or isotopic ratios of specific molecules, in such a way as to minimize the sensitivity of the results to variations in the conditions under which the spectra were acquired.
3) Tune a laser successively to a collection of frequencies by altering one or more laser parameters such as the current and temperature, each of these frequencies being sufficiently close to a resonant frequency of an optical cavity that efficient optical injection can be achieved with high duty cycle.
4) Carry out the desired laser tuning with the aid of an ancillary wavelength monitor within a feedback loop.

C) Ring-Down Binning in FSR Hopping Mode

C1) Summary

In FSR-CRDS as described above, the cavity length is kept fixed while the laser current is swept over an interval such that the laser is tuned across many cavity free spectral ranges. From time to time, ring-downs will occur and the fine laser current at the time of each ring-down is recorded. Ring-downs are initiated by removing the optical power provided to the ring-down cavity. Such control of the optical power is provided by a semiconductor optical amplifier (SOA) at the output of the laser. In this way, ring-downs are initiated such that the laser current is not changed while ring-downs take place. If the rate at which the laser current is swept is sufficiently rapid, the laser temperature does not change appreciably throughout the process and the laser frequency is determined essentially by the laser current. We describe a method for maintaining a mapping between the laser current and the laser frequency which is informed by the fact that ring-downs can occur only when the laser frequency is a multiple of the cavity free spectral range. This mapping allows the ring-down events to be binned by FSR index, which may be converted into actual frequencies by using the known cavity free spectral range and using spectroscopy to identify the absolute frequency from the position of a known spectral feature.

One approach to binning the ring-down events by laser current is to collect a large number of ring-downs and to use a clustering algorithm to group together those events for which the laser currents are sufficiently close together that they are likely to be from a single cavity mode. Since clusters are often identified based on the number of events that fall close to each other, such methods are not useful when there are relatively few events at each FSR so that the clustering is not apparent. When collecting a spectrum using FSR-CRDS, the laser current is swept repeatedly over a wide range. The number of sweeps is chosen so that there is a reasonable probability that there is at least one ring-down at each cavity FSR so that the spectroscopic fitter has enough information to determine the concentration. Under such conditions, it can be difficult to reliably assign an FSR index to each ring-down, since the number of points at a particular FSR can be few or even zero. If there are also occasional outliers which do not lie on the expected grid of frequencies, these can introduce errors into the concentration estimates which are difficult to filter out. It may be argued that one can simply wait for more scans to be taken so that the clusters become better defined, but this may lead to an unacceptable slow-down in the data acquisition rate and an inability to follow rapid changes in concentration of the analyte.

Since the mapping between laser current and laser frequency does not change significantly on the timescale at which spectra are collected, we can learn this relationship over many spectra (perhaps with the help of a clustering algorithm based on the ring-down events aggregated over many spectra). We may then use the relationship to make FSR index assignments to ring-downs that subsequently occur at known laser currents, even though the data for a single spectrum are too sparse to define clusters. In the algorithm that is described below, the need for a sophisticated clustering algorithm is removed by using the fact that the longitudinal cavity resonances are equally spaced in frequency, and the observation that the relationship between laser current and frequency for a DFB laser is usually only weakly non-linear. A low-degree polynomial model for the relationship between laser current and frequency (or more conveniently FSR index) is calculated and used for the index assignment. The coefficients of this model can be updated slowly as data are collected in order to track any long-term drifts in the relationship due to laser aging or other causes.

C2) Description of the Method

Suppose that a collection of ring-downs are collected with a cavity of fixed length under the conditions of constant laser temperature described above, so that the laser frequency is essentially determined by the laser current. Let us denote the laser current at the k'th ring-down by $I_k$ and suppose that the frequency of the laser for this ring-down is $v_k$. We aim to determine the functional relationship $v(I)$ for the laser by using the fact that the only allowed frequencies for ring-downs are separated by the cavity free spectral range $\Delta v_{FSR}$. It is convenient to normalize the laser frequency by the cavity free spectral range and to define the FSR index relative to some reference cavity resonance frequency $v_0$ by $$f = (v - v_0)/\Delta v_{FSR}.$$

Corresponding to the k'th ring-down which took place at current $I_k$, we then have an integer $$f_k = f(I_k) \equiv [v(I_k) - v_0]/\Delta v_{FSR}.$$

From measurements made on distributed feedback (DFB) lasers, it is known that the relationship between the laser frequency and laser current at constant laser temperature is approximately linear, and that the weak non-linearity over a typical current scan range of ±20 mA can be adequately represented by a low order polynomial such as a quadratic with an error which is small compared to the cavity free spectral range of ~0.02 cm$^{-1}$. This indicates that a relationship of the form $f(I) = A + BI + CI^2$ for parameters A, B and C may be found such that $f(I_k)$ are close to integers, and such that consecutive integers correspond to consecutive longitudinal mode resonance frequencies of the cavity. We may express the method for determining the parameters as an optimization by selecting an objective function which is large when the values $f_k$ are integers and small when they are not. A suitable function satisfying this condition is $\Sigma_k \cos[2\pi f(I_k)]$. It is easy to perform the maximization over A analytically since $$\Sigma_k \cos[2\pi f(I_k)] = \Sigma_k \cos[2\pi(A + BI_k + CI_k^2)] = \cos(2\pi A)\Sigma_k \cos[2\pi(BI_k + CI_k^2)] - \sin(2\pi A)\Sigma_k \sin[2\pi(BI_k + CI_k^2)].$$

If we set $$A = -\frac{1}{2\pi}\arg\sum_k \exp[i2\pi(BI_k + CI_k^2)]$$

this maximizes the expression over A, yielding $$\Sigma_k \cos[2\pi f(I_k)] = |\Sigma_k \exp[i2\pi(BI_k + CI_k^2)]|.$$

It remains to find values of B and C which maximize this reduced objective function. Although this function has multiple local maxima, it is found that the global maximum is broad and easy to locate. Once the optimal parameter values have been found, it is possible to track their values over time by using a steepest ascents algorithm based on calculating the gradient of the square of the reduced objective function and making a small step in that direction as spectra are collected. More explicitly, if we define $$R = \Sigma_k \exp[i2\pi(BI_k + CI_k^2)]$$

$$S = \Sigma_k I_k \exp[i2\pi(BI_k + CI_k^2)]$$

and $$T = \Sigma_k I_k^2 \exp[i2\pi(BI_k + CI_k^2)]$$

then $$\frac{\partial |R|^2}{\partial B} = 4\pi \mathrm{Im}(RS^*) \quad \text{and} \quad \frac{\partial |R|^2}{\partial C} = 4\pi \mathrm{Im}(RT^*)$$

Once we have the values of the parameters A, B and C, we can bin ring-downs on the basis of the laser current I at the time of the ring-down by evaluating f(I) and finding the nearest integer.

C3) Example

Ring-down data were collected using FSR hopping mode with a methane analyzer. The fine laser current was swept over range of approximately 33 mA, which caused the laser frequency to scan over 50 cavity free spectral ranges or 1 cm$^{-1}$. The full range of laser current was normalized by linearly mapping it to the interval −0.5 to +0.5 for the purpose of the following calculations.

A collection of 2500 ring-down events were gathered with the cavity length fixed, and the normalized laser current $I_k$ was recorded for each event. From these, the reduced objective function was computed using $$|\Sigma_k \exp[i2\pi(BI_k + CI_k^2)]|.$$

Figure 14:
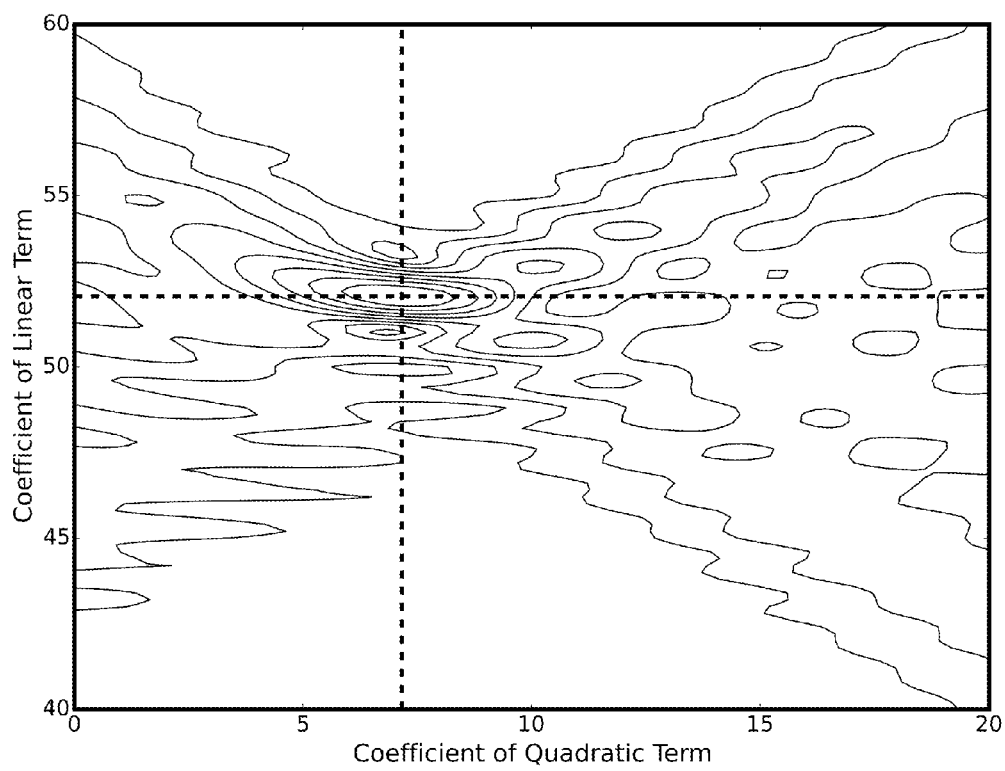
FIG. 14 is a contour plot relating to an example where FSR index is determined for 2500 ring-down events.
Figure 15:
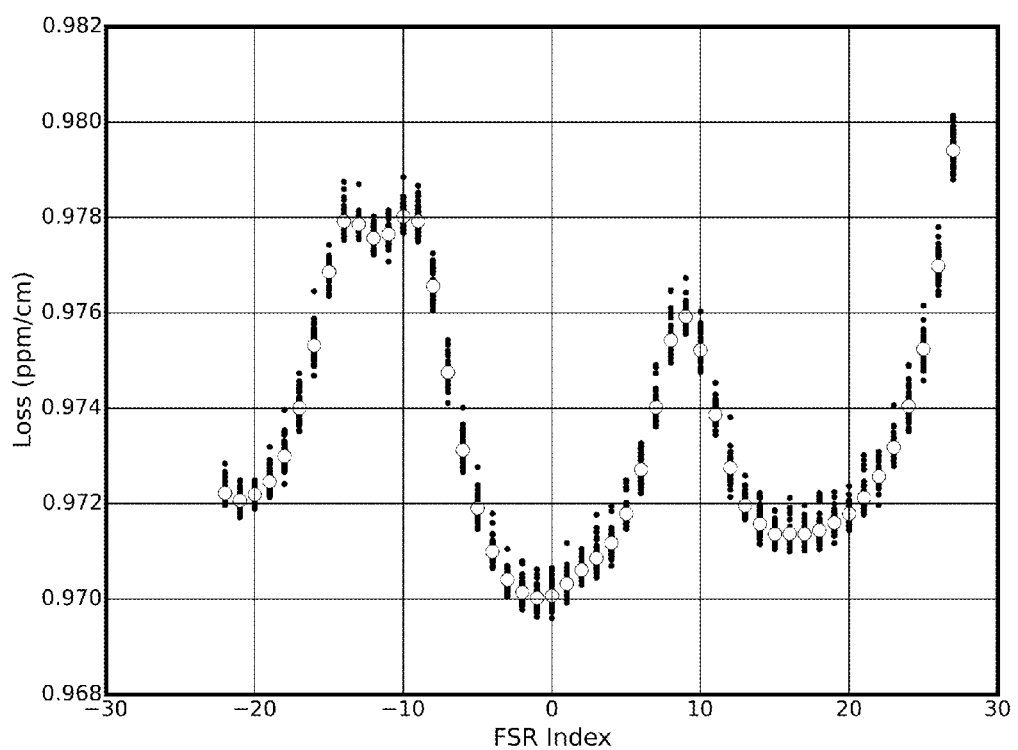
FIG. 15 is a loss vs. FSR index plot relating to the example of FIG. 14.

FIG. 14 shows a contour plot of this function for all the ring-downs. There is a well-defined global maximum at B=52.1 and C=7.16 (at the intersection of the dashed lines on the plot). Using these values to compute A, the resulting mapping was used to bin the ring-down events by FSR index. The loss values for the individual ring-downs are plotted against FSR index together with the mean loss in each in FIG. 15. This spectrum illustrates how data with a correct (relative) frequency axis can be obtained without the use of a wavelength monitor.

Figure 16:
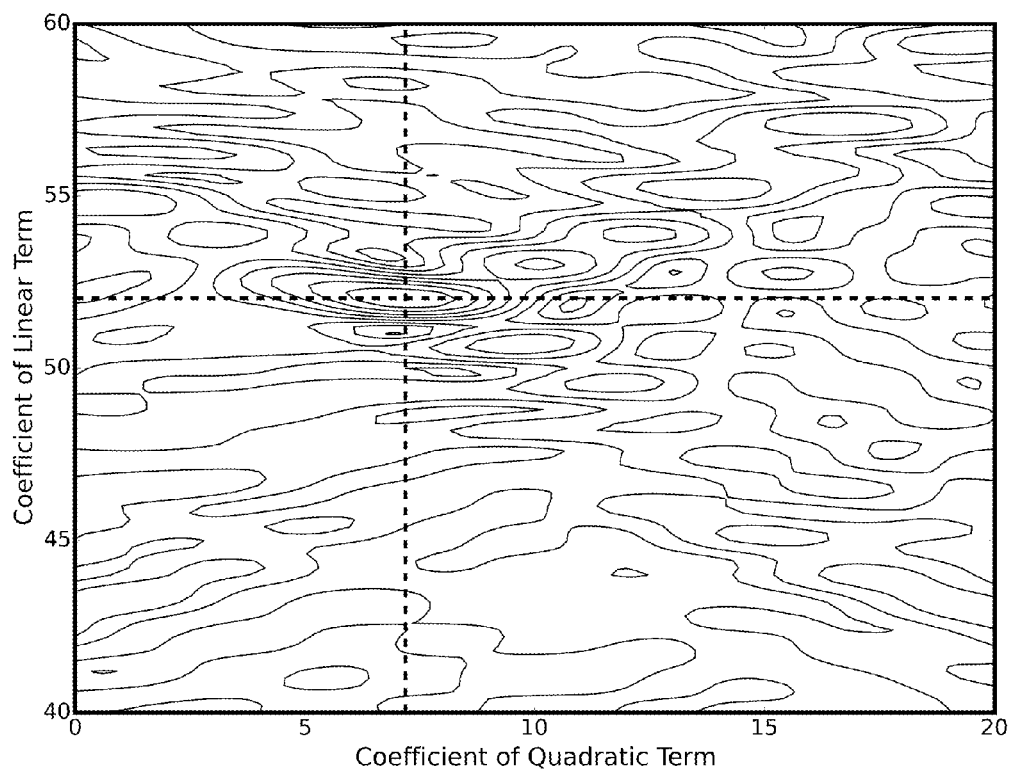
FIG. 16 is a contour plot relating to the first 100 ring-down events of the example of FIG. 14.

In FIG. 16, the contour plot of reduced objective function is plotted using only the first 100 ring-downs from the data set. Although the subsidiary maxima are more pronounced, the global maximum is still well-defined and is located at B=52.0 and C=7.18 (at the intersection of the dashed lines on the plot). This illustrates that the algorithm is able to provide information for updating the coefficients of the model even from a relatively small number of ring-downs, which is useful for tracking slow changes in the model.

C4) Conclusions and Exemplary Embodiments

We provide a method for assigning frequencies to ring-down events which are known to occur only on a regularly spaced grid of frequencies.

A quantity such as laser current (which is related to the laser frequency) is measured at each ring-down. The method uses the way in which this quantity is distributed to determine the relationship between it and the frequency. This relationship may be updated as data are collected, thus allowing slow changes in the relationship to be tracked.

The method allows for the construction of spectrometers which can operate without an accurate wavelength monitor, but which still allow for the precise measurement of the shapes of spectral features.

An exemplary embodiment is a method for performing cavity enhanced optical spectroscopy, where the method includes:

1) providing an optical resonator that defines a first set of cavity modes having a free spectral range (FSR) and which is configured to include a sample for analysis, where the optical resonator is configured to passively provide relative frequency stability of the first set of cavity modes of 10% or less of the FSR in a time period of about 1 second;

2) providing an optical source configured to deliver optical radiation to the optical resonator;

3) providing a detector configured to receive an absorbance signal from the optical resonator that is responsive to optical absorption in the sample;

4) collecting spectrograms from the sample by sweeping a frequency of the optical source through two or more frequencies of the first set of cavity modes and recording the absorbance signal;

5) computing an analysis output from the spectrogram by assuming that data points in the spectrogram are evenly spaced in frequency; and 6) providing an FSR calibration between one or more optical source parameters and an FSR index (e.g., as described above in section C using laser current as the optical source parameter).

Some embodiments can further include relating the FSR index to a frequency reference, thereby providing absolute frequency information for the spectrograms. The FSR calibration can be updated over time, to account for drift in parameter values etc.

The one or more optical source parameters can include any parameter which varies with optical wavelength. Because the FSR of the cavity provides for a highly accurate measurement of the difference between two frequencies, and because the resulting spectrogram provide a highly accurate measurement of the absolute optical frequency, the remaining requirement is to determine which cavity mode has been excited; that is, to measure the FSR index as described above. This can be done with a parameter that depends on the central wavelength of the optical source. This parameter can be either a control parameter, such as laser wavelength, or a measurement parameter, such as the reflection from or transmission through an optical etalon or other optical component. If a single parameter is used, the parameter must vary monotonically (but not necessarily linearly) with wavelength over the spectral region of interest.

Consider for example the reflection of a plane-parallel piece of optically transmitting glass. The reflection of the front and back surfaces interfere to create a reflection whose magnitude varies sinusoidally with optical frequency. The period of the sinusoid is inversely proportional to the thickness of the glass; for reasonable thicknesses on the order of 1 mm, the reflected signal may increase or decrease monotonically over the spectral region of interest. Although the reflected signal has a nonlinear dependence on wavelength, and may drift over time, it can still be used to determine the FSR index of the optical source. This can be regarded as an example where a relatively crude wavelength monitor (i.e., one that does not provide an absolute frequency reference because of drift etc.) is sufficient to determine the FSR index of the ring-down events.

In cases where the optical source is a semiconductor laser, one of the optical source parameters can be laser current.

The FSR calibration can include fitting a discrete polynomial model to measured laser current. Updating the FSR calibration can include updating the coefficients of the discrete polynomial model as data is gathered during operation. Here a 'discrete polynomial model' refers to fitting a curve to data points ($x_i$, $y_i$) where the $x_i$ values are assumed to be integer multiples of a base value. This base value is the cavity FSR in this case.

The preferred embodiments of sections A and B above can be combined with FSR calibration as in section C in any or all combinations. For example, a wavelength monitor can be used to determine the absolute wavelength or frequency of one or more of the cavity modes to provide the FSR calibration.

The invention claimed is:

1. A method for performing cavity enhanced optical spectroscopy, the method comprising:
    providing an optical resonator that defines a first set of cavity modes having a free spectral range (FSR) and which is configured to include a sample for analysis, wherein the optical resonator is configured to passively provide relative frequency stability of the first set of cavity modes of 10% or less of the FSR in a time period of about 1 second;
    providing an optical source configured to deliver optical radiation to the optical resonator;
    providing a detector configured to receive an absorbance signal from the optical resonator that is responsive to optical absorption in the sample;
    collecting spectrograms from the sample by sweeping a frequency of the optical source through two or more frequencies of the first set of cavity modes and recording the absorbance signal;
    computing an analysis output from the spectrogram by assuming that data points in the spectrogram are evenly spaced in frequency; and
    providing an FSR calibration between one or more optical source parameters and an FSR index.

2. The method of claim 1, further comprising relating the FSR index to a frequency reference, whereby absolute frequency information for the spectrograms is provided.

3. The method of claim 1, further comprising updating the FSR calibration over time.

4. The method of claim 3, wherein the one or more optical source parameters include a parameter which varies with optical wavelength.

5. The method of claim 4, wherein the optical source is a semiconductor laser and wherein the one or more optical source parameters include laser current.

6. The method of claim 5, wherein the providing an FSR calibration comprises fitting a discrete polynomial model to measured laser current.

7. The method of claim 6, wherein the updating the FSR calibration comprises updating coefficients of the discrete polynomial model as data is gathered during operation.

8. The method of claim 1, wherein the optical source is configured to provide relative frequency stability of the optical radiation of 10% or less of the FSR in a time period of about 1 second.

9. The method of claim 1, wherein the optical source is configured to provide relative frequency precision of the optical radiation of 10% or less of the FSR in a time period of about 1 second.

10. The method of claim 1, further comprising providing frequency control of the optical source to facilitate tuning the frequency of the optical source to align with two or more of the first set of cavity modes during the collecting spectrogram.

11. The method of claim 10, wherein the optical source is a semiconductor laser and wherein the frequency control of the optical source comprises both current control and temperature control.

12. The method of claim 1, wherein the method for performing cavity enhanced optical spectroscopy comprises a method selected from the group consisting of: cavity ringdown spectroscopy, cavity enhanced absorption spectroscopy, and integrated cavity output spectroscopy.

13. The method of claim 1, wherein the computing an analysis output comprises determining an integrated absorption by fitting a spectral line shape model to the spectrogram.

14. The method of claim 1, wherein the providing the FSR calibration comprises use of a wavelength monitor to determine absolute wavelength or frequency of one or more of the cavity modes.

* * * * *